(12) United States Patent
Jung et al.

(10) Patent No.: US 12,048,771 B2
(45) Date of Patent: Jul. 30, 2024

(54) MULTIFUNCTIONAL MICROSTRUCTURE PATCH

(71) Applicants: INDUSTRY-ACADEMIC COOPERATION FOUNDATION, YONSEI UNIVERSITY, Seoul (KR); JUVIC INC., Seoul (KR)

(72) Inventors: Hyungil Jung, Seoul (KR); Huisuk Yang, Seoul (KR)

(73) Assignees: INDUSTRY-ACADEMIC COOPERATION FOUNDATION, YONSEI UNIVERSITY, Seoul (KR); JUVIC INC, Seoul (KR)

( * ) Notice: Subject to any disclaimer, the term of this patent is extended or adjusted under 35 U.S.C. 154(b) by 659 days.

(21) Appl. No.: 17/283,480

(22) PCT Filed: Oct. 4, 2019

(86) PCT No.: PCT/KR2019/013073
§ 371 (c)(1),
(2) Date: Apr. 7, 2021

(87) PCT Pub. No.: WO2020/076017
PCT Pub. Date: Apr. 16, 2020

(65) Prior Publication Data
US 2022/0008353 A1    Jan. 13, 2022

(30) Foreign Application Priority Data
Oct. 8, 2018 (KR) .................... 10-2018-0119642

(51) Int. Cl.
*A61K 9/70* (2006.01)
*A61K 9/00* (2006.01)
*A61M 5/42* (2006.01)
*A61M 37/00* (2006.01)

(52) U.S. Cl.
CPC ........... *A61K 9/7092* (2013.01); *A61M 5/422* (2013.01); *A61M 37/0015* (2013.01); *A61K 9/0021* (2013.01); *A61M 2037/0023* (2013.01); *A61M 2202/048* (2013.01)

(58) Field of Classification Search
None
See application file for complete search history.

(56) References Cited

U.S. PATENT DOCUMENTS

| 2005/0106226 A1* | 5/2005 | Cormier ............... A61K 9/7084 424/449 |
| 2021/0016070 A1* | 1/2021 | Cho .................. A61M 37/0015 |

FOREIGN PATENT DOCUMENTS

| KR | 20150138647 | 12/2015 |
| KR | 20170108049 | 9/2017 |
| KR | 20170138664 | 12/2017 |
| KR | 20180056411 | 5/2018 |
| WO | WO 2007/007128 | 1/2007 |

OTHER PUBLICATIONS

International Search Report and Written Opinion issued in Corresponding PCT Application No. PCT/KR2019/013073, dated Jan. 23, 2020 (English Translation provided).

* cited by examiner

*Primary Examiner* — H. Sarah Park
(74) *Attorney, Agent, or Firm* — NORTON ROSE FULBRIGHT US LLP (57) ABSTRACT

A multifunctional microstructure patch is provided. The multifunctional microstructure patch, according to one embodiment of the present invention, comprises: a base layer having an opening part formed in the center thereof; a plurality of microstructures formed on one surface of the base layer and comprising a first drug; and a cover layer detachably bonded on the other surface of the base layer along the periphery of the opening part, and formed so as to cover the opening part.

18 Claims, 9 Drawing Sheets

MULTIFUNCTIONAL MICROSTRUCTURE PATCH

CROSS-REFERENCE TO RELATED APPLICATIONS

This application is a national phase application under 35 U.S.C. § 371 of International Application No. PCT/KR2019/013073, filed Oct. 4, 2019, which claims priority to and the benefit of Korean Patent Application No. 10-2018-0119642, filed Oct. 8, 2018. The contents of the referenced patent applications are incorporated into the present application by reference.

FIELD OF THE DISCLOSURE

The present invention relates to a microstructure patch, and more particularly, to a multifunctional microstructure patch for injecting different drugs after attaching a microstructure patch to skin.

DESCRIPTION OF RELATED ART

A subcutaneous drug injection method is one of methods commonly used in treatment of various diseases and drug delivery. Compared to an oral drug delivery method in which a drug is absorbed while passing through a digestive system in a body, subcutaneous drug injection has the following advantages. That is, drug denaturation and decomposition rate are low, drug delivery efficiency in a body is high, side effects through quantitative drug delivery are reduced, or the like. Currently, as the subcutaneous drug injection method, hypodermic needles having various diameters are widely used.

The conventional hypodermic needles are used in most drug delivery methods. However, when the hypodermic needle is inserted into skin, skin damage and pain are inevitable due to the length and diameter of the hypodermic needle, and side effects such as allergic reactions due to metal materials and phobia of needles due to pain occur. In particular, in the case of a specific disease requiring repeated drug injections for a short period of time, it is impossible to perform an injection on the same site due to a wound that occurs when previous subcutaneous injections are performed, and thus, there are problems such as a decrease in patient convenience and a decrease in drug injection efficiency.

In order to solve the problems of the conventional hypodermic needle, a microstructure having a micro size suitable for performing the subcutaneous drug injection has been developed. The microstructure is a micro-sized structure that can solve problems such as pain, trauma, and reduced patient convenience of the conventional hypodermic needle, and particularly, a biodegradable microstructure can deliver drugs with minimal invasiveness without pain, which is a research field that has recently been in the spotlight.

Here, when microstructures are manufactured in the form of a "patch" attached to skin, it is possible to perform the drug delivery function of the injection without pain, and thus, drugs that the conventional patch cannot deliver can be newly delivered. In this case, the conventional microstructures are attached to the skin together with the patch in a form arranged on a support.

However, the microstructure patch is attached to the skin in a certain area, and thus, it is difficult to inject different drugs. That is, in the case of sequentially administering different drugs to the skin or administering different drugs at a certain time interval, since a state where a micro-patch corresponding to an initially administered drug is continuously attached should be maintained, the microstructure patch is not suitable for administering different drugs.

Meanwhile, a process of inserting a tool such as a hypodermic needle or catheter into skin to administer drugs in a body or collect body fluids may cause pain or discomfort to a patient. In this case, a local anesthetic is administered to relieve the patient's pain.

However, when the local anesthetic is administered using the conventional hypodermic needle, the above-described problems may occur, and when a cream type local anesthetic is used, a great deal of time is required for anesthesia. In addition, when the local anesthetic is administered in the form of a patch as described above, the patch should be continuously attached until the anesthetic through the patch is absorbed into the skin. Therefore, there is a problem that additional measures, such as injection of the hypodermic needle or catheter, cannot be performed while the patch is attached.

In addition, micropores are formed in the skin according to the injection of the hypodermic needle or catheter, and thus, separate measures are required to disinfect or press the site after removing them from the skin.

SUMMARY OF THE INVENTION

The present invention is directed to providing a multifunctional microstructure patch capable of administering different drugs while using a patch form.

Moreover, the present invention is directed to providing a multifunctional microstructure patch capable of performing a treatment painlessly by local anesthesia during injection and safely protecting a corresponding site after the injection.

An aspect of the present invention provides a multifunctional microstructure patch including a base layer having an opening part, a plurality of microstructures formed on one surface of the base layer and including a first drug, and a cover layer detachably bonded to the other surface of the base layer along a periphery of the opening part and formed so as to cover the opening part.

The multifunctional microstructure patch may further include a protective layer bonded to a surface of the cover layer facing the base layer and having a size smaller than or equal to that of the opening part.

At least a portion of the cover layer may be separated from the base layer before a hypodermic needle is inserted through the opening part.

The cover layer may be re-bonded to the base layer after the hypodermic needle is removed.

The first drug may include a local anesthetic selected from the group consisting of cocaine, procaine, chloroprocaine hydrochloride, tetracaine, dibucaine, lidocaine, mepivacaine, benzocaine, bupivacaine, and a combination thereof.

The local anesthetic may be applied on a surface of the microstructure or embedded in the microstructure.

The cover layer may include a peeling portion protruding from a portion of an outer periphery and the peeling portion may not be coated with an adhesive.

The cover layer may include an adhesive portion on which an adhesive is formed along a periphery of the protective layer.

An adhesive may be formed on one surface of the base layer.

The protective layer may include cotton or gauze.

The protective layer may include a disinfectant.

The disinfectant may include ethanol or isopropyl alcohol.

The first drug may include a biocompatible material or a biodegradable material.

The multifunctional microstructure patch may further include a second base layer attached to skin in the opening part after the base layer is attached to skin and the cover layer is separated from the base layer, and a plurality of second microstructures formed on one surface of the second base layer and including a second drug different from the first drug.

The cover layer may include an adhesive portion on which an adhesive is formed along a periphery of the opening part.

The second base layer may be larger than the opening part, and the second microstructure may be formed to be disposed in the opening part.

The second base layer may be smaller than or equal to the opening part.

The first drug and second drug may include a biocompatible material or a biodegradable material.

The opening part may be formed at a center of the base layer, formed in a "C" or "c" shape, or formed in a circular, elliptical, curved, or polygonal shape, and may have one side formed to communicate with an outer periphery of the base layer.

Another aspect of the present invention provides a multifunctional microstructure patch including a first base layer having an opening part, a plurality of first microstructures formed on one surface of the first base layer and including a first drug, a second base layer attached to skin in the opening part after the first base layer is attached to skin, and a plurality of second microstructures formed on one surface of the second base layer and including a second drug different from the first drug.

In a multifunctional microstructure patch according to one embodiment of the present invention, an opening part is formed in a base layer and a cover layer covering the opening part is attached to be detachable from the base layer. Accordingly, an injection insertion or attachment of other patches is possible in a state where the base layer is not completely separated from the skin and only the cover layer is separated, drugs can be additionally administered or additional measures can be taken even in a state where the patch is attached, and thus, convenience and efficiency can be improved.

In the multifunctional microstructure patch according to one embodiment of the present invention, a microstructure including a local anesthetic is formed on one surface of the base layer. Accordingly, when the local anesthetic is administered, anesthesia can be quickly performed without pain, and thus, the injection insertion can be performed without pain.

In addition, in the multifunctional microstructure patch according to one embodiment of the present invention, the cover layer includes a protective layer including a disinfectant. Accordingly, by simply re-bonding the cover layer to the base layer after the injection is completed, micropores formed by the injection can be sterilized or acupressure can be performed on the micropores, and thus, separate measures are not necessary, and it is possible to improve ease of use.

DETAILED DESCRIPTION OF THE INVENTION

Hereinafter, embodiments of the present invention will be described in detail with reference to the accompanying drawings so that those of ordinary skill in the art may easily implement the present invention. The present invention may be implemented in various different forms and is not limited to the embodiments described herein. In the drawings, parts irrelevant to the description are omitted in order to clearly describe the present invention, and the same reference numerals are assigned to the same or similar components throughout the specification.

Figure 1:
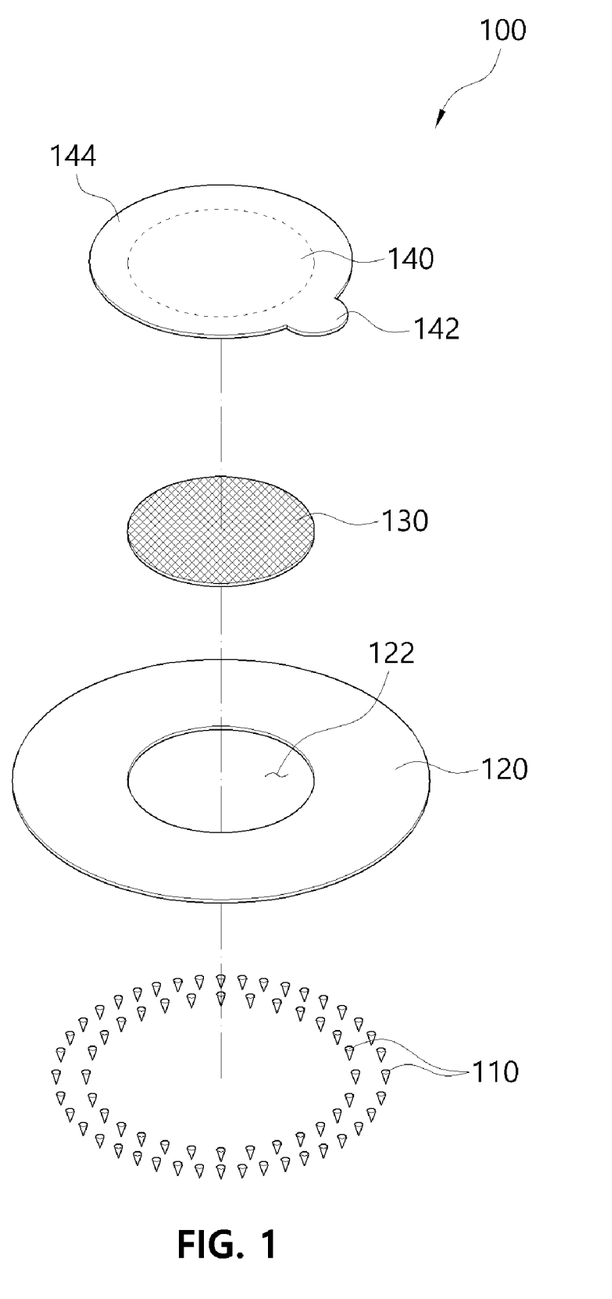
FIG. 1 is an exploded perspective view of a multifunctional microstructure patch according to a first embodiment of the present invention.
Figure 2:
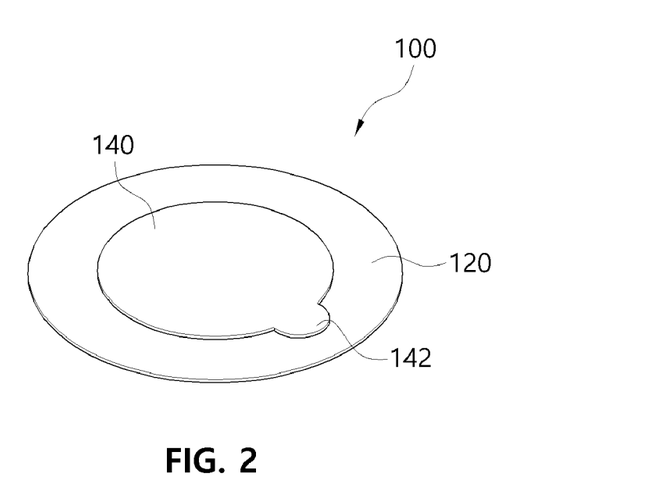
FIG. 2 is a perspective view of an upper portion of the multifunctional microstructure patch according to the first embodiment of the present invention.
Figure 3:
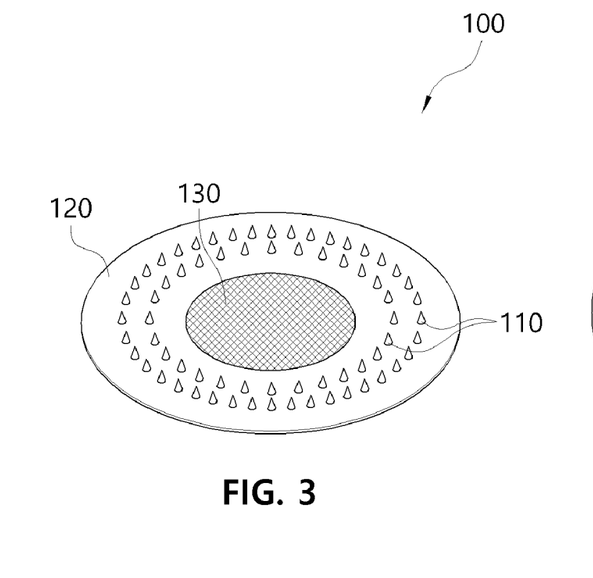
FIG. 3 is a perspective view of a lower portion of the multifunctional microstructure patch according to the first embodiment of the present invention.

Hereinafter, multifunctional microstructure patches according to embodiments of the present invention will be described in more detail with reference to the accompanying drawings. FIG. 1 is an exploded perspective view of a multifunctional microstructure patch according to a first embodiment of the present invention, FIG. 2 is a perspective view of an upper portion of the multifunctional microstructure patch according to the first embodiment of the present invention, and FIG. 3 is a perspective view of a lower portion of the multifunctional microstructure patch according to the first embodiment of the present invention.

Referring to FIG. 1, a multifunctional microstructure patch 100 according to the first embodiment of the present invention includes microstructures 110, a base layer 120, and a cover layer 140.

In the present invention, the multifunctional microstructure patch 100 is for administering additional drugs or taking additional measures through an opening part 122 of the base layer 120 in a state of being attached to skin. More specifically, the multifunctional microstructure patch 100 is for sequentially administering different drugs to the skin or administering drugs at a certain time interval.

In this case, a drug to be administered to the skin for the first time may be provided by the multifunctional microstructure patch 100, and a drug to be administered afterwards may be provided by a hypodermic needle or another microstructure patch.

For example, when different drugs are administered sequentially, an immune response enhancing material may be administered through the multifunctional microstructure patch 100, and then, vaccine vaccination injection may be performed.

When different drugs are administered at a certain time interval, after a local anesthetic substance is administrated through the microstructures 110, additional measures such as vaccination vaccine injection or laser treatment may be performed.

Here, the additional measures refer to measures such as collecting a body fluid or disinfecting the skin or performing acupressure after removing the hypodermic needle. That is, the additional measures may include measures that may be performed in a state where the multifunctional microstructure patch 100 is attached to the skin.

Accordingly, in the state where the multifunctional microstructure patch 100 is attached to the skin, it is possible to administer additional drugs or take additional measures, and thus, it is possible to improve convenience and efficiency of use.

In the present specification, administration of a drug using the hypodermic needle after the multifunctional microstructure patch 100 is described as the first embodiment, and administration of a drug using another micro-patch after the multifunctional microstructure patch 100 is described as a second embodiment.

Here, in the case of the first embodiment, the multifunctional microstructure patch 100 includes a local anesthetic or an immune response enhancing material, and the drug to be administered using a hypodermic needle may be a preventive vaccine.

In the case of the second embodiment, the multifunctional microstructure patch 100 includes an immune response enhancing material, and the drug to be administered using another micro-patch may be a vaccination vaccine.

The multifunctional microstructure patch 100 according to the first embodiment is for administration of additional drugs or collection of the body fluid using the hypodermic needle. In this case, the multifunctional microstructure patch 100 is attached to an injection site so that the local anesthetic is injected into the skin to relieve pain when a hypodermic needle is inserted into the skin for the purpose of injecting the drugs or collecting the body fluids. That is, the multifunctional microstructure patch 100 may include a local anesthetic but is not limited thereto. However, for convenience of description, hereinafter, it will be described that the multifunctional microstructure patch 100 includes the local anesthetic.

Here, the example of the hypodermic needle is used as a tool inserted into the skin, but it is not particularly limited and anything that causes pain to the patient may be applied, such as a catheter. That is, in the present specification, the "injection" means inserting a tool, which can cause pain to a patient, such as the hypodermic needle or catheter, into the skin.

However, the present invention is not limited to the injection and may be used to alleviate pain prior to procedures such as laser, tattooing, or peeling or various cosmetic and medical actions that cause pain.

Accordingly, even when the local anesthetic itself is administered, anesthesia can be performed quickly and painlessly, and the insertion of the hypodermic needle or catheter can be performed without pain by local anesthesia.

Here, the local anesthetic is an anesthetic agent for partially anesthetizing a body part and is not particularly limited. For example, the local anesthetic may be selected from the group consisting of cocaine, procaine, chloroprocaine hydrochloride, tetracaine, dibucaine, lidocaine, mepivacaine, benzocaine, bupivacaine, and a combination thereof.

In addition, a material forming the microstructure 110 in the present invention includes a biocompatible or biodegradable material. As used herein, the term "biocompatible material" refers to a material that is substantially non-toxic to a human body, is chemically inactive, and is not immunogenic. In the present specification, the term "biodegradable material" refers to a material that can be degraded by body fluids or microorganisms in a living body.

Specifically, for example, biocompatible and/or biodegradable materials that may be used in the present invention are polyester, polyhydroxyalkanoate (PHAs), poly($\alpha$-hydroxyacid), poly($\beta$-hydroxyacid), poly(3-hydrosicbutyrate-co-valerate; PHBV), poly(3-hydroxypropionate; PHP), poly(3-hydroxyhexanoate; PHH), poly(4-hydroxyacid), poly(4-hydroxybutyrate), poly(4-hydroxyvalerate), poly(4-hydroxyhexanoate), poly(esteramide), polycaprolactone, polylactide, polyglycolide, poly(lactide-co-glycolide; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazens, PHA-PEG, ethylene vinyl alcohol copolymer (EVOH), polyurethane, silicone, polyester, polyolefin, polyisobutylene and ethylene-alphaolefin copolymer, styrene-isobutylene-styrene triblock copolymers, acrylic polymers and copolymers, vinyl halide polymers and copolymers, polyvinyl chloride, polyvinyl ether, polyvinyl methyl ether, polyvinylidene halide, polyvinylidene fluoride, polyvinylidene chloride, polyfluoroalkene, polyperfluoroalkene, polyacrylonitrile, polyvinyl ketone, polyvinyl aromatics, polystyrene, polyvinyl ester, polyvinyl acetate, ethylene-methyl methacrylate copolymer, acrylonitrile-styrene copolymer, ABS resin and ethylene-vinyl acetate copolymer, polyamide, alkyd resin, polyoxymethylene, polyimide, polyether, polyacrylate, polymethacrylate, polyacrylic acid-co-maleic acid, chitosan, dextran, cellulose, heparin, hyaluronic acid, alginate, inulin, starch, or glycogen, and preferably, are polyester, polyhydroxyalkanoate (PHAs), poly($\alpha$-hydroxy acid), poly($\beta$-hydroxy acid), poly(3-hydrosoxybutyrate-co-valerate; PHBV), poly(3-hydroxypropionate; PHP), poly(3-hydroxyhexanoate; PHH), poly(4-hydroxyacid), poly(4-hydroxybutyrate), poly(4-hydroxyvalerate), poly(4-hydroxyhexanoate), poly(esteramide), polycaprolactone, polylactide, polyglycolide, poly(lactide-co-glycolide; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazene, PHA-PEG, chitosan, dextran, cellulose, heparin, hyaluronic acid, alginate, inulin, starch, or glycogen.

The microstructure 110 is formed on one surface of the base layer 120. That is, the microstructure 110 may be formed on a surface of the base layer 120 which is attached to the skin. In this case, the microstructure 110 may be formed by spotting after applying a viscous composition to the base layer 120. Here, the viscous composition may be formed by a biocompatible or biodegradable material as described above, or a drug that is injectable into the body, and a combination thereof.

As described above, the material used in the present invention to prepare the microstructure is the viscous composition. In the present specification, the term "viscous composition" refers to a composition having the ability to form the microstructure by changing a shape.

In addition, the microstructure 110 includes the local anesthetic. In this case, the microstructure 110 may be formed by coating a surface formed of the biocompatible or biodegradable material with the local anesthetic.

Alternatively, the microstructure 110 may contain the local anesthetic. That is, the microstructure 110 may be first formed with a viscous local anesthetic, and then the surface may be formed using a viscous biocompatible or biodegradable material.

In addition, the microstructure 110 may have a circular horizontal cross section. In this case, the microstructure 110 may be formed in a circular shape having a predetermined area at a portion to be bonded to the base layer 120. In addition, the microstructure 110 may include a pointed tip portion at a portion to be implanted in the skin.

The base layer 120 is a portion attached to the skin and is formed in a plate shape, and an opening part 122 is formed therein. That is, when the base layer 120 is attached to the skin, the skin may be exposed through the opening part 122. Here, the opening part 122 may form a space for the hypodermic needle 20 which will be inserted into the skin.

In this case, the opening part 122 may be formed at a center of the base layer 120 or may be formed in one side. Here, when the opening part 122 is formed at the center of the base layer 120, the base layer 120 may have an "O" shape. In addition, when the opening part 122 is provided in one side of the base layer 120, and in particular, formed to communicate with the outer periphery of the base layer 120, the base layer 120 may have a "C" or "⊂" shape. However, a location and a shape of the opening part 122 are not particularly limited and may be formed variously.

Figure 4:
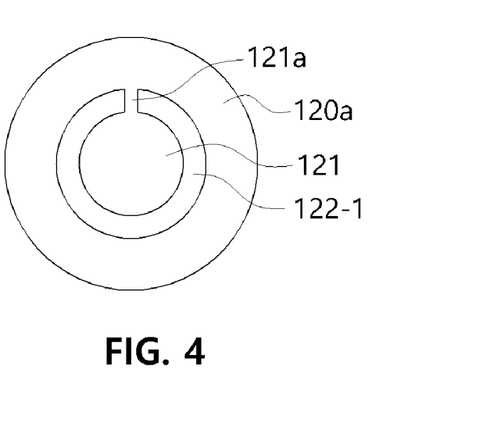
FIG. 4 is a plan view illustrating a first modification example of an opening part in the multifunctional microstructure patch according to the first embodiment of the present invention.
Figure 5:
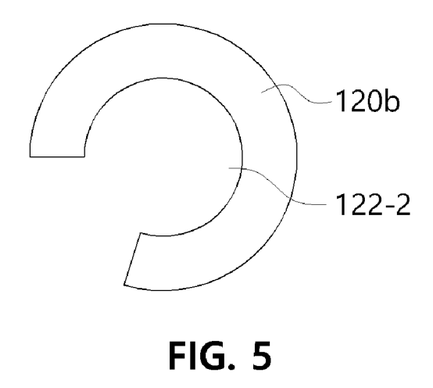
FIG. 5 is a plan view illustrating a second modification example of the opening part in the multifunctional microstructure patch according to the first embodiment of the present invention.
Figure 6:
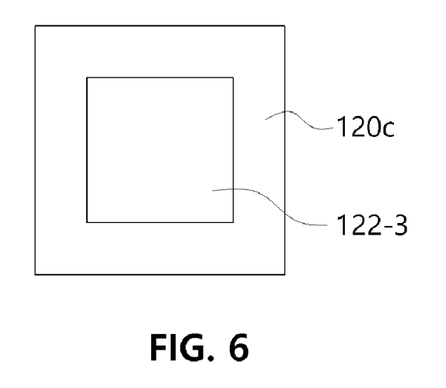
FIG. 6 is a plan view illustrating a third modification example of the opening part in the multifunctional microstructure patch according to the first embodiment of the present invention.

FIG. 4 is a plan view illustrating a first modification example of the opening part in the multifunctional microstructure patch according to the first embodiment of the present invention, FIG. 5 is a plan view illustrating a second modification example of the opening part in the multifunctional microstructure patch according to the first embodiment of the present invention, and FIG. 6 is a plan view illustrating a third modification example of the opening part in the multifunctional microstructure patch according to the first embodiment of the present invention.

Referring to FIG. 4, an opening part 122-1 may be formed at a center of a base layer 120a, and an extension part 121 may be formed therein. Here, the extension part 121 may be connected to the base layer 120a, which is located at an outer side, through the extension part 121a on one side of the opening part 122-1. That is, the opening part 121-1 may be formed in a "C" shape or a "⊂" shape at the center of the base layer 120a.

In this case, the microstructure 110 may be formed only on the extension part 121. Optionally, of course, the microstructure 110 may be formed on both the extension part 121 and the base layer 120a around the outer periphery thereof.

Accordingly, when it is necessary to perform additional measures outside a specific area of the skin to be injected with a drug, it is possible to easily perform the drug injection and additional measures.

Referring to FIG. 5, an opening part 122-2 may be formed to communicate with the outside at an outer periphery of a base layer 120b. Here, the base layer 120b may be formed in a form in which one side is open due to the opening part 122-2. That is, the base layer 120b may have an overall shape of a "C" or a "⊂" shape.

Accordingly, it is possible to minimize the limitations of additional measures caused by a portion of the base layer according to the type of additional measures.

Referring to FIG. 6, an opening part 122-3 may be formed in a quadrangle shape. In this case, a base layer 120c may be formed in a quadrangle shape similar to the opening part 122-3. However, the present invention is not limited thereto, and the opening part 122-3 may be formed in any one of a circular shape, an elliptical shape, a curved shape, and a polygonal shape. In this case, the base layer 120c may be formed in the same shape as the opening part 122-3 or may be formed in a different shape.

Accordingly, in response to drug administration and additional measures, it is possible to expose the skin in a suitable form and administer the drug, thereby improving the convenience of use.

In addition, the base layer 120 may be formed with an adhesive that is formed on one surface of the base layer 120 to be attached to the skin. That is, the multifunctional microstructure patch 100 may have the adhesive formed on one surface of the base layer 120 so as to be attached and fixed to the skin.

Here, the adhesive useable in the present invention may include a rubber-based adhesive, an acrylic-based adhesive, a silicone-based adhesive, and a urethane-based adhesive but is not particularly limited thereto.

In this case, the base layer 120 may be made of various materials. For example, the base layer 120 may be composed of a polymer material, a metal, ceramics, glass, a film, an adhesive patch, a vinyl-based material, silicone, a fiber sheet, nanofibers, or paper but is not limited thereto. In addition, the base layer 120 may be composed of two or more materials and may be composed of a mixture of the two or more materials or the form of a separate layer but is not limited thereto. In addition, the base layer 120 may have a flexible shape, and a shape of the base layer 120 may change according to a pressure applied to the skin.

Referring to FIGS. 1 and 2, the cover layer 140 is bonded to a surface of the base layer 120 opposite to the microstructures 110. Here, the cover layer 140 is detachably bonded along the periphery of the opening part 122 and formed to cover the opening part 122.

In this case, the cover layer 140 may include an adhesive portion 144 in which an adhesive is formed along a periphery of a protective layer 130 as described below. The adhesive portion 144 may be formed outside the protective layer 130 at regular intervals.

The adhesive formed on the adhesive portion 144 may be made of the same material as that of the adhesive formed on one surface of the base layer 120. As an example, the adhesive may include a rubber-based adhesive, an acrylic-based adhesive, a silicone-based adhesive, and a urethane-based adhesive but is not particularly limited thereto.

In addition, the cover layer 140 may include a peeling portion 142 protruding from a portion of an outer periphery. Here, the peeling portion 142 may be formed to protrude outward on the same plane as the cover layer 140. In this case, the peeling portion 142 may not be coated with an adhesive to easily separate the cover layer 140 from the base layer 120.

In addition, the cover layer 140 may be made of the same material as that of the base layer 120. For example, the cover layer 140 may be made of a polymer material, a metal, ceramics, glass, a film, an adhesive patch, a vinyl-based material, silicone, a fiber sheet, nanofibers, or paper.

The multifunctional microstructure patch 100 according to the first embodiment of the present invention may further include the protective layer 130.

Referring to FIGS. 1 and 3, the protective layer 130 is bonded to a surface of the cover layer 140 facing the base layer 120. Here, the protective layer 130 is for disinfecting the skin or performing acupressure after a hypodermic needle is removed, and has a size smaller than or equal to that of the opening part 122.

For example, the protective layer 130 may be formed of cotton or gauze but is not limited thereto. That is, the protective layer 130 may be a woven fabric made of a fibrous material and may have a soft texture when in contact with the skin.

In addition, the protective layer 130 may include a disinfectant to disinfect micropores formed in the skin by a hypodermic needle. Here, the disinfectant that can be used in the present invention may include ethanol or isopropyl alcohol but is not limited thereto.

Figure 7:
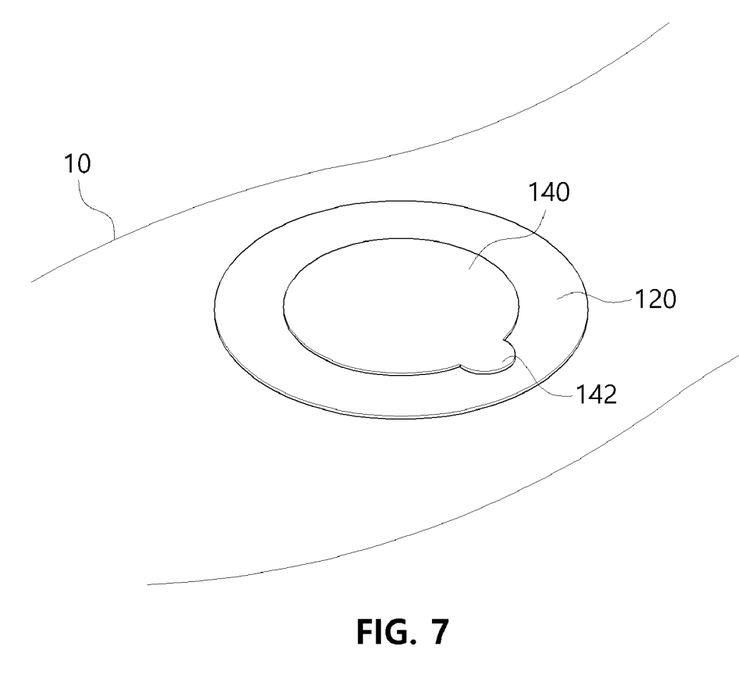
FIG. 7 is a perspective view illustrating a state where the multifunctional microstructure patch according to the first embodiment of the present invention is attached to skin.
Figure 10:
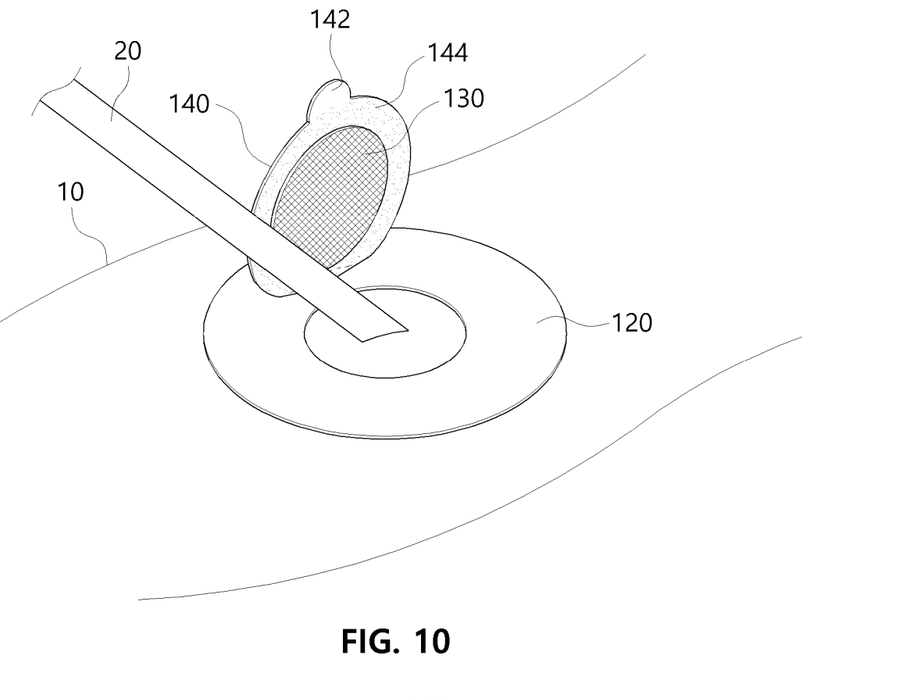
FIG. 10 is a perspective view illustrating a state where a hypodermic needle is inserted into skin in FIG. 9.
Figure 11:
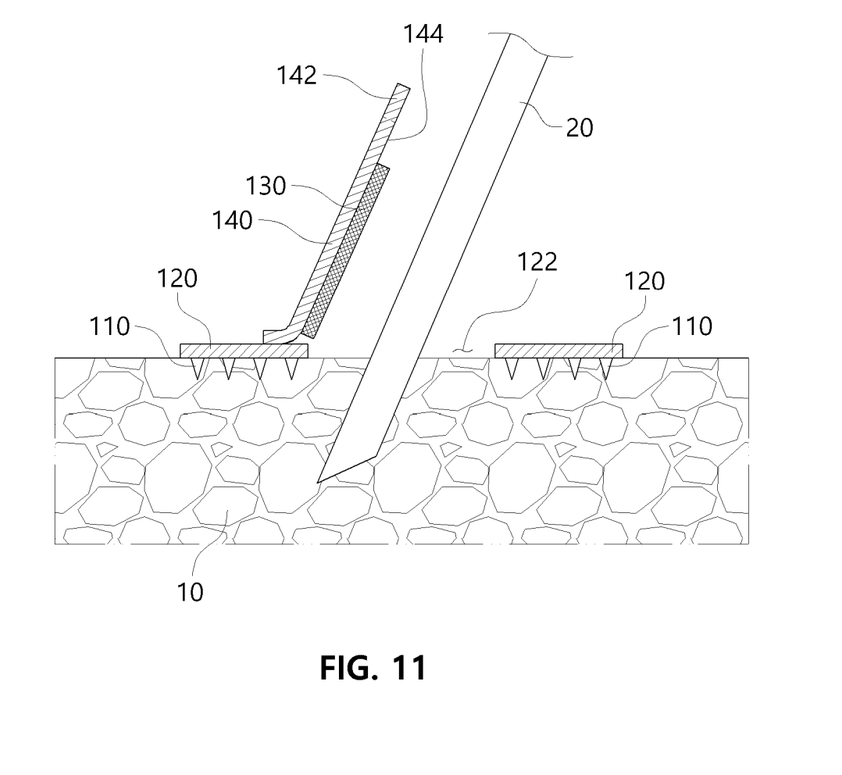
FIG. 11 is a cross-sectional view of FIG. 10.

Hereinafter, an example of using the multifunctional microstructure patch 100 according to the first embodiment of the present invention will be described in detail with reference to FIGS. 7 to 11. FIG. 7 is a perspective view illustrating a state where the multifunctional microstructure patch according to the first embodiment of the present invention is attached to skin, FIG. 8 is a cross-sectional view of FIG. 7, FIG. 9 is a perspective view illustrating a state where the cover layer is separated in FIG. 7, FIG. 10 is a perspective view illustrating a state where a hypodermic needle is inserted into skin in FIG. 9, and FIG. 11 is a cross-sectional view of FIG. 10.

Referring to FIG. 7, the multifunctional microstructure patch 100 is attached to a skin site for injection to administer drugs or take additional measures. In this case, an upper surface of the base layer 120 is uniformly pressed so that the plurality of microstructures 110 can be uniformly inserted into the skin.

Figure 8:
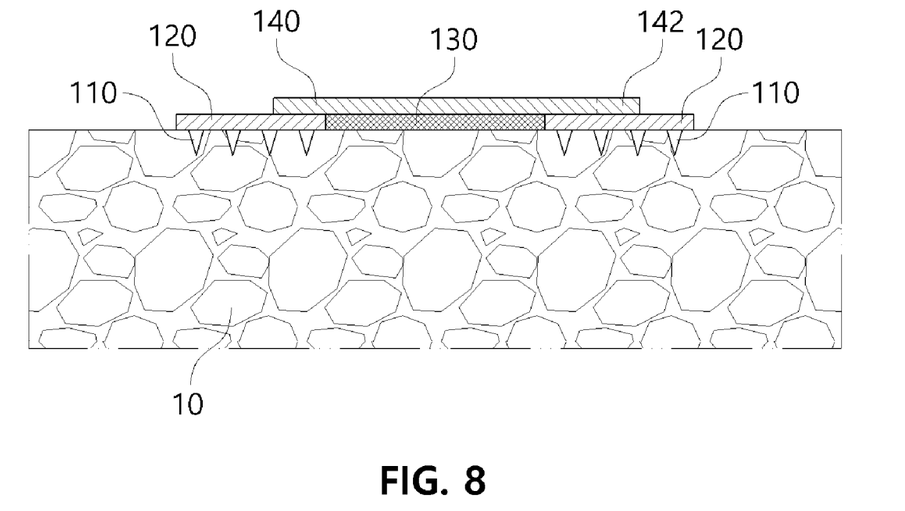
FIG. 8 is a cross-sectional view of FIG. 7.

Referring to FIG. 8, as the base layer 120 is attached to the skin 10, the microstructures 110 are inserted into the skin 10. In this state, the microstructures 110 break down within the skin, and a local anesthetic contained in the microstructures 110 is absorbed by the skin. Therefore, the corresponding site is anesthetized. Here, it is described that the microstructures 110 include the local anesthetic but is not limited thereto.

Figure 9:
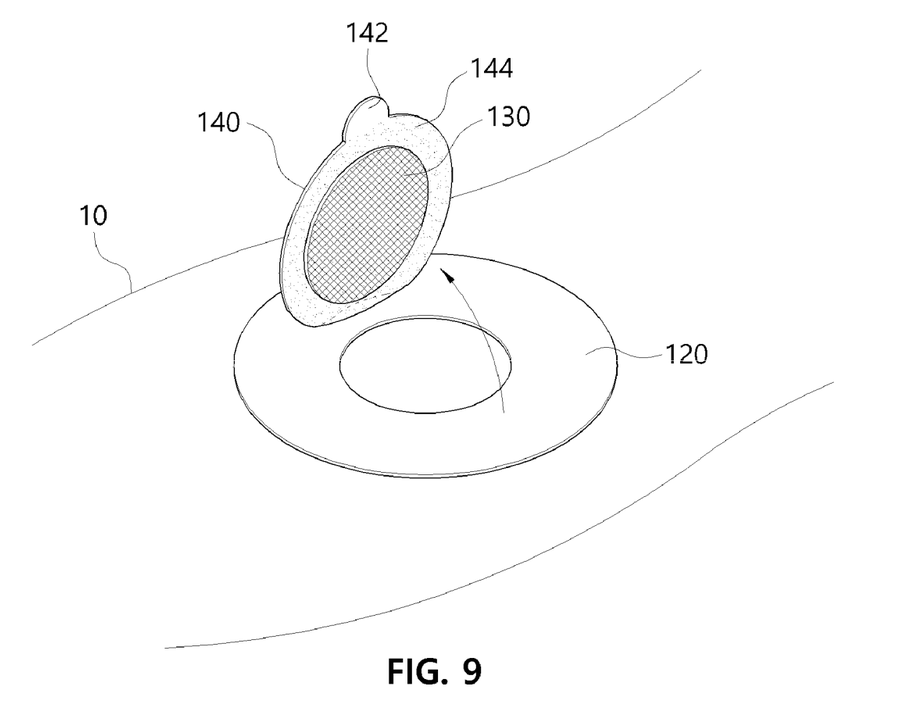
FIG. 9 is a perspective view illustrating a state where a cover layer is separated in FIG.

Referring to FIG. 9, an insertion space of the hypodermic needle 20 is formed in a state where the corresponding site is anesthetized. To this end, at least a portion of the cover layer 140 is separated from the base layer 120 so that the opening part 122 is opened. In this case, since a portion of the cover layer 140 may be slightly separated first using the peeling portion 142 in which the adhesive is not formed, the cover layer 140 may be easily separated from the base layer 120.

Referring to FIG. 10, the hypodermic needle 20 is inserted through the opening part 122 that is open in order to inject a drug different from that included in the microstructures 110 or to collect a body fluid. In this case, the cover layer 140 may maintain a partially bonded state from the base layer 120 or may be entirely separated from the base layer 120.

Referring to FIG. 11, in a state where a portion of the cover layer 140 is separated from the base layer 120 and the opening part 122 is open, the hypodermic needle 20 is inserted into the exposed skin to inject the drug or collect the body fluid.

Accordingly, the insertion for the injection is possible in a state where the base layer 120 is not completely separated from the skin and only the cover layer 140 is separated. Therefore, it is possible to take additional measures even in a state where the multifunctional microstructure patch 100 is attached, and thus, it is possible to improve the convenience and efficiency.

When the drug injection or the collection of the body fluid is completed through the hypodermic needle 20 inserted into the skin, the hypodermic needle 20 is removed from the skin. Immediately after the hypodermic needle 20 is removed as described above, the cover layer 140 separated from the base layer 120 so that the opening part 122 is opened is re-bonded to the base layer 120.

In this case, while the protective layer 130 is in contact with the skin, micropores formed in the skin site by the hypodermic needle 20 may be disinfected by the disinfectant included in the protective layer 130. In addition, when the body fluid is collected, an acupressure effect may be provided by pressing a portion of the protective layer 130.

Accordingly, by simply re-bonding the cover layer 140 to the base layer 120 after the injection is completed, the micropores formed in the skin by the injection can be sterilized or the acupressure can be performed thereon, and thus, separate measures are not necessary, and it is possible to improve ease of use.

Meanwhile, a multifunctional microstructure patch 200 according to a second embodiment is for administering an additional drug using another micro-patch.

Figure 12:
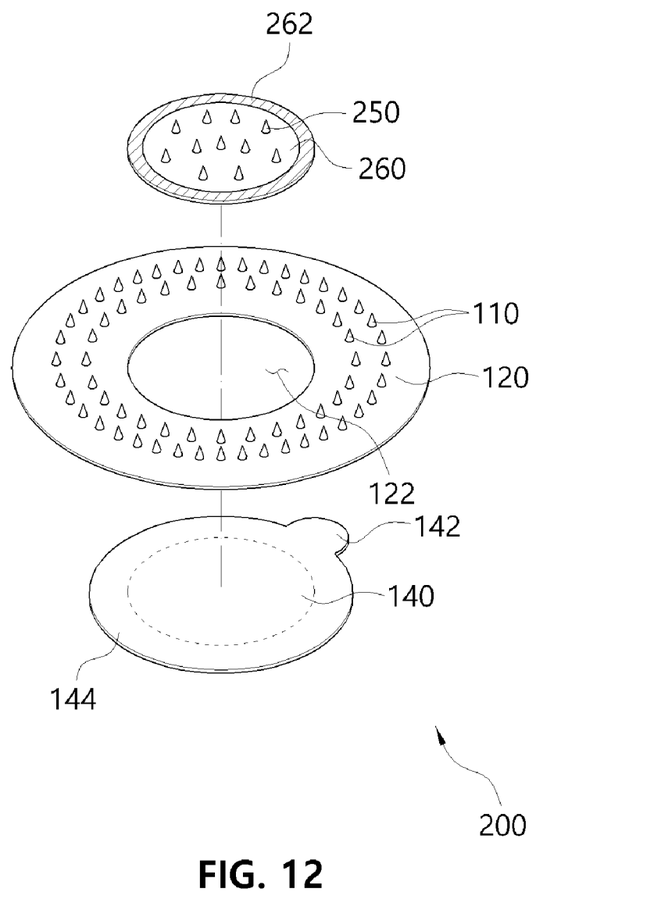
FIG. 12 is an exploded perspective view of a multifunctional microstructure patch according to a second embodiment of the present invention.
Figure 13:
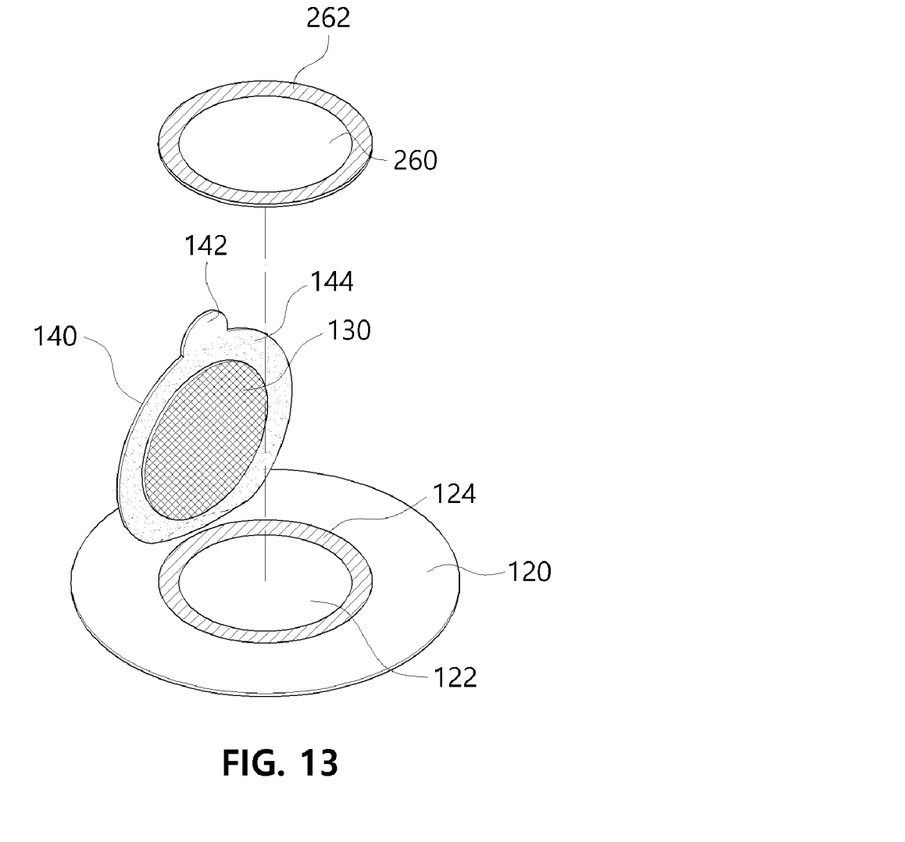
FIG. 13 is a perspective view of an upper portion of the multifunctional microstructure patch according to the second embodiment of the present invention.
Figure 14:
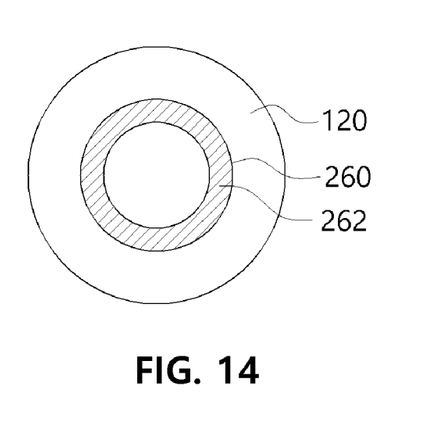
FIG. 14 is a plan view illustrating a state where a first micro-patch and a second micro-patch are coupled when a second base layer is larger than an opening part of a first base layer in FIG. 13.
Figure 15:
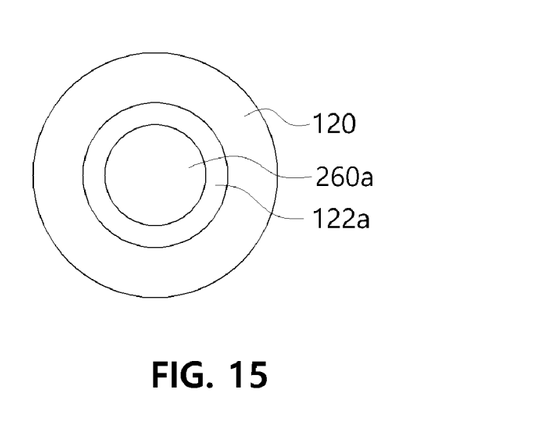
FIG. 15 is a plan view illustrating a state where the first micro-patch and the second micro-patch are coupled when the second base layer is smaller than the opening part of the first base layer in FIG. 13.

FIG. 12 is an exploded perspective view of the multifunctional microstructure patch according to the second embodiment of the present invention, FIG. 13 is a perspective view of an upper portion of the multifunctional microstructure patch according to the second embodiment of the present invention, FIG. 14 is a plan view illustrating a state where a first micro-patch and a second micro-patch are coupled when a second base layer is larger than an opening part of a first base layer in FIG. 13, and FIG. 15 is a plan view illustrating a state where the first micro-patch and the second micro-patch are coupled when the second base layer is smaller than the opening part of the first base layer in FIG. 13.

Referring to FIGS. 12 and 13, the multifunctional microstructure patch 200 includes microstructures 110, a base layer 120, a cover layer 140, second microstructures 250, and a second base layer 260. Here, the microstructures 110 and the base layer 120 are a first microstructure patch, and the second microstructures 250 and the second base layer 260 are a second microstructure patch. The first microstructure patch is the same as the multifunctional microstructure patch 100 according to the first embodiment, and thus, detailed descriptions thereof will be omitted.

In this case, the second microstructure patch is secondarily attached to the skin in a state where the first microstructure patch is attached to the skin and provides a drug different from that of the first microstructure patch.

The second microstructures 250 may be formed of a biocompatible or biodegradable material similar to the microstructures 110 but may include the drug different from that of the microstructures 110.

The second microstructures 250 are formed on one surface of the second base layer 260. That is, the second microstructures 250 may be formed on a surface of the second base layer 260 which is attached to the skin. In this case, the second microstructures 250 are administrated to the skin in a state where the base layer 120 is attached to the skin, and thus, the second microstructures 250 may be formed to be disposed within the opening part 122.

Here, it will be understood that the second microstructures 250 have identical or similar characteristics to those of the microstructures 110 unless otherwise specified.

The second base layer 260 is a portion attached to the skin within the opening part 122 and may be formed in a plate shape. In this case, the second base layer 260 may be attached to the skin within the opening part 122 after the base layer 120 is attached to the skin and the cover layer 140 is separated from the base layer 120.

Here, it will be understood that the second base layer 260 has identical or similar characteristics to those of the base layer 120 unless otherwise specified.

Referring to FIGS. 13 and 14, the second base layer 260 may be formed larger than the opening part 122. That is, the second base layer 260 may be formed to cover the entire opening part 122.

In this case, a coupling portion 262 may be formed along an outer periphery of one surface of the second base layer 260. Here, the coupling portion 262 is a portion coupled to the base layer 120 and may correspond to an adhesive portion 124 formed along the outer periphery of the opening part 122 on the upper surface of the base layer 120.

In addition, the second base layer 260 may be formed with an adhesive on one surface of the second base layer 260 so as to be attached and fixed to the skin. In this case, since the adhesive is also formed on the coupling portion 262, the coupling portion 262 may be adhered to the adhesive portion 124 of the base layer 120.

Accordingly, when the second microstructure patch is attached to the opening part 122 of the first microstructure patch, the second microstructure patch may be adhered to the first microstructure patch. Therefore, two separately provided microstructure patches can be stably attached to the skin.

Here, in the cover layer 140, the adhesive portion 144 in which an adhesive is formed along the periphery of the opening part 122 may be adhered to the adhesive portion 124 of the base layer 120.

In addition, when the second base layer 260 is smaller than the opening part 122, an adhesive may be formed on the entire surface of the cover layer 140 including the adhesive portion 144. Accordingly, the cover layer 140 may cover the second base layer 260 after the second base layer 260 is attached to the skin, and thus, may adhere the first microstructure patch and the second microstructure patch.

Referring to FIG. 15, a second base layer 260a may be smaller than or equal to the opening part 122. In particular, when the second base layer 260a is smaller than the opening part 122, in the second base layer 260a, the base layer 120 and a space 122a may be formed in the opening part 122.

Accordingly, when the second microstructure patch is attached to the opening part 122 of the first microstructure patch, the second microstructure patch may be easily attached to the opening part 122.

Hereinafter, an example of using the multifunctional microstructure patch 200 according to the second embodiment of the present invention will be described in detail with reference to FIGS. 16 to 18.

Figure 16:
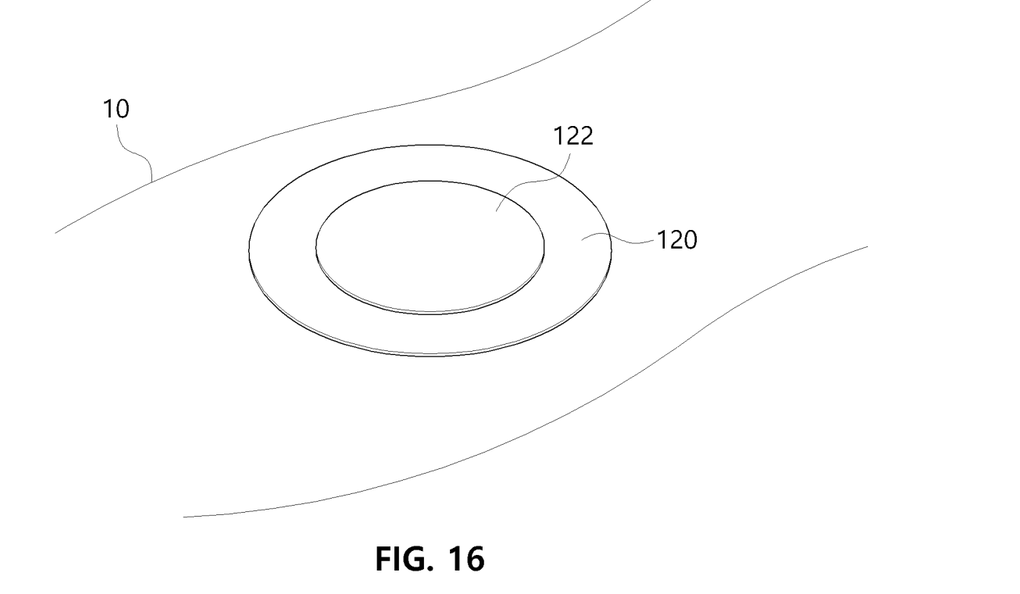
FIG. 16 is a perspective view illustrating a state where the first micro-patch of the multifunctional microstructure patch according to the second embodiment of the present invention is attached to skin.
Figure 17:
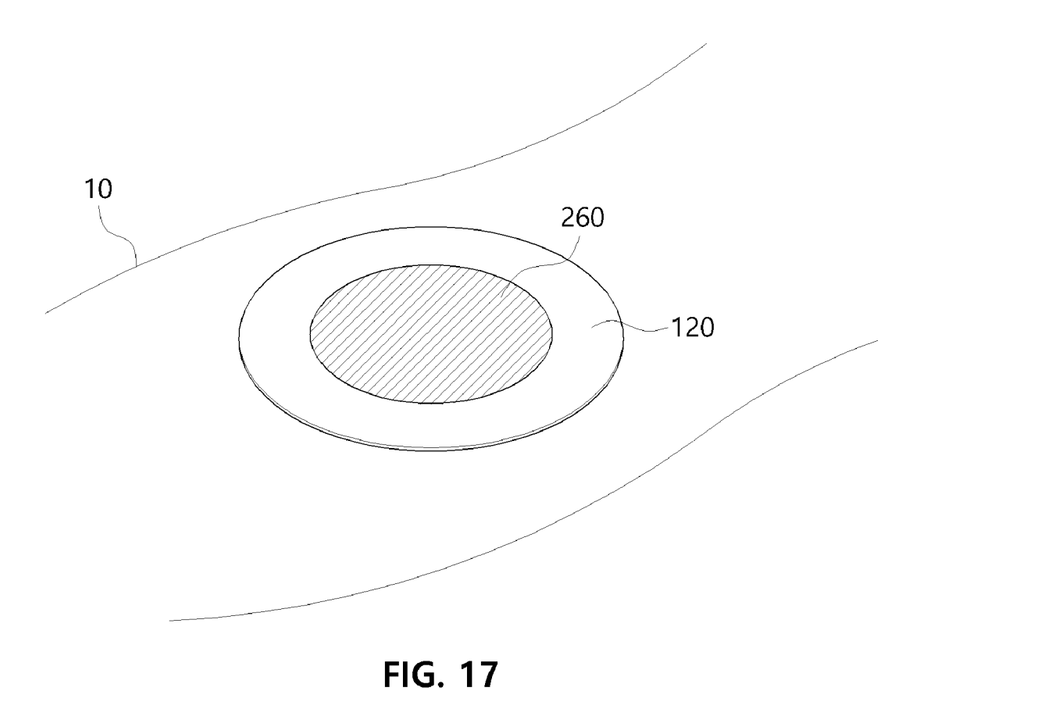
FIG. 17 is a perspective view illustrating a state where the second micro-patch is attached to skin in FIG. 16.
Figure 18:
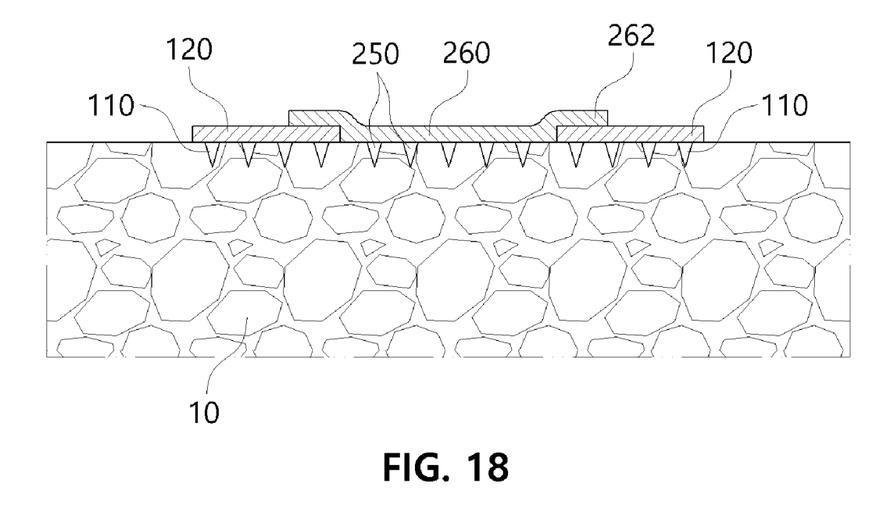
FIG. 18 is a cross-sectional view of FIG. 17.

FIG. 16 is a perspective view illustrating a state in which the first micro-patch of the multifunctional microstructure patch according to the second embodiment of the present invention is attached to skin, FIG. 17 is a perspective view illustrating a state in which the second micro-patch is attached to skin in FIG. 16, and FIG. 18 is a cross-sectional view of FIG. 17.

Referring to FIG. 16, the first microstructure patch is attached to a site of the skin 10 for administering a drug. In this case, the upper surface of the base layer 120 is uniformly pressed so that the plurality of microstructures 110 can be uniformly inserted into the skin 10.

Immediately after the first microstructure patch is attached or when a certain time has elapsed after the attachment, at least a portion of the cover layer 140 is removed so that the second microstructure patch is additionally attached to the skin 10 through the opening part 122 of the base layer 120.

Referring to FIG. 17, the second microstructure patch is attached to the opening part 122 of the base layer 120. In this case, the upper surface of the second base layer 260 is uniformly pressed so that the plurality of second microstructures 250 can be uniformly inserted into the skin 10.

Here, when the second base layer 260 is larger than the opening part 122, the cover layer 140 is completely removed from the base layer 120. In this case, the coupling portion 262 of the second base layer 260 is uniformly pressed so that the coupling portion 262 protruding outward of the opening part 122 is adhered to the adhesive portion 124 on the upper surface of the base layer 120.

Meanwhile, when the second base layer 260 is smaller than or equal to the opening part 122, the cover layer 140 is not completely removed from the base layer 120. In this case, after the second microstructure patch is attached to the opening part 122, the cover layer 140 is re-bonded to the base layer 120 again.

Accordingly, the second base layer 260 is easily attached within the opening part 122 and at the same time, the second base layer 260 is completely covered and pressed by the cover layer 140, and thus, the second base layer 260 may be stably adhered to the skin 10.

Referring to FIG. 18, as the base layer 120 and the second base layer 260 are attached to the skin 10, the microstructures 110 and the second microstructures 250 are inserted into the skin 10. That is, the microstructures 110 and the second microstructures 250 may be attached to the skin 10 sequentially or at predetermined time intervals. In this case, the base layer 120 and the second base layer 260 may maintain an adhesive state through the coupling portion 262.

As a result, the second microstructure patch can be attached into the opening part 122 in a state where the first microstructure patch is completely not separated from the skin 10 and only the cover layer 140 is separated. Accordingly, even in the state where the first microstructure patch is attached, an additional drug may be administered using different microstructure patches, and thus, it is possible to improve the convenience and efficiency.

Although the embodiments of the present invention are described above, a spirit of the present invention is not limited to the embodiments of the present specification, and those skilled in the art who understand the spirit of the present invention may easily propose other embodiments by addition, change, deletion, addition, or the like of constituent elements within the scope of the same idea, which fall within the scope of the present invention.

The invention claimed is:

1. A multifunctional microstructure patch comprising:
   a base layer having an opening part;
   a plurality of microstructures formed on one surface of the base layer and including a first drug;
   a cover layer detachably bonded to the other surface of the base layer along a periphery of the opening part and formed so as to cover the opening part; and
   a protective layer bonded to a surface of the cover layer facing the base layer and having a size smaller than or equal to that of the opening part.

2. The multifunctional microstructure patch of claim 1, wherein at least a portion of the cover layer is configured to be separated from the base layer.

3. The multifunctional microstructure patch of claim 2, wherein the cover layer is configured to be re-bonded to the base layer.

4. The multifunctional microstructure patch of claim 1, wherein the first drug includes a local anesthetic selected from the group consisting of cocaine, procaine, chloroprocaine hydrochloride, tetracaine, dibucaine, lidocaine, mepivacaine, benzocaine, bupivacaine, and a combination thereof.

5. The multifunctional microstructure patch of claim 4, wherein the local anesthetic is comprised on a surface of the microstructure or embedded in the microstructure.

6. The multifunctional microstructure patch of claim 1, wherein the cover layer includes a peeling portion protruding from a portion of an outer periphery and the peeling portion is not coated with an adhesive.

7. The multifunctional microstructure patch of claim 1, wherein the cover layer includes an adhesive portion comprising an adhesive, wherein the adhesive is comprised along a periphery of the protective layer.

8. The multifunctional microstructure patch of claim 1, wherein an adhesive is comprised on one surface of the base layer.

9. The multifunctional microstructure patch of claim 1, wherein the protective layer includes cotton or gauze.

10. The multifunctional microstructure patch of claim 1, wherein the protective layer includes a disinfectant.

11. The multifunctional microstructure patch of claim 10, wherein the disinfectant includes ethanol or isopropyl alcohol.

12. The multifunctional microstructure patch of claim 1, wherein the first drug includes a biocompatible material or a biodegradable material.

13. The multifunctional microstructure patch of claim 1, further comprising:
    a second base layer configured to be attached to skin in the opening part; and
    a plurality of second microstructures comprised on one surface of the second base layer and including a second drug different from the first drug.

14. The multifunctional microstructure patch of claim 13, wherein the cover layer includes an adhesive portion comprising an adhesive, wherein the adhesive is comprised along a periphery of the opening part.

15. The multifunctional microstructure patch of claim 13, wherein the second base layer is larger than the opening part, and the second microstructure is disposed in the opening part.

16. The multifunctional microstructure patch of claim 13, wherein the second base layer is smaller than or equal to the opening part.

17. The multifunctional microstructure patch of claim 13, wherein the first drug and second drug include a biocompatible material or a biodegradable material.

18. The multifunctional microstructure patch of claim 1, where the opening part is comprised at a center of the base layer, wherein the opening comprises a "C" or " ⊂ " shape a circular shape, an elliptical shape, a curved shape, or a polygonal shape.

* * * * *